(12) United States Patent
Geczy

(10) Patent No.: US 7,754,715 B2
(45) Date of Patent: Jul. 13, 2010

(54) SUSTAINED-RELEASE ORAL MOLSIDOMINE COMPOSITION FOR TREATING ATHEROSCLEROSIS

(75) Inventor: Jozsef-Michel Geczy, Brussels (BE)

(73) Assignee: Therabel Pharmaceuticals Limited, Loughrea Co, Galway (IE)

( * ) Notice: Subject to any disclaimer, the term of this patent is extended or adjusted under 35 U.S.C. 154(b) by 605 days.

(21) Appl. No.: 10/599,634

(22) PCT Filed: Apr. 1, 2005

(86) PCT No.: PCT/EP2005/003531

§ 371 (c)(1),
(2), (4) Date: Nov. 21, 2006

(87) PCT Pub. No.: WO2005/107761

PCT Pub. Date: Nov. 17, 2005

(65) Prior Publication Data

US 2007/0212413 A1    Sep. 13, 2007

(30) Foreign Application Priority Data

Apr. 5, 2004    (FR) .................................. 04 03534

(51) Int. Cl.
*A61K 31/535* (2006.01)
(52) U.S. Cl. ...................... 514/236.2; 424/468; 514/824
(58) Field of Classification Search .................. 424/468
See application file for complete search history.

(56) References Cited

U.S. PATENT DOCUMENTS

| 5,385,937 A | 1/1995 | Stamler et al. |
| 6,472,390 B1 * | 10/2002 | Stamler et al. ........... 514/236.5 |
| 2003/0045522 A1 * | 3/2003 | Geczy .................... 514/236.2 |

OTHER PUBLICATIONS

Kinoshita, M., Long-Term Effects of Molsidomine on exercise tolerance in patients with exertional angina pectoris, Japanese Circulation Journal, vol. 47, Dec. 1983, pp. 1398-1405.*
Grodzinska et al "Therapeutic Effects of Molsidomine No-Donor in Patients with Atherosclerosis Obliterans of the Lower Limbs", Journal of Drug Development, pp. 39-46, 1991.
Roland et al "Local Delivery of No-Donor Molsidomine Post-PTO . . . ", Journal of the European Society for Vascular Surgery, pp. 236-233, 2002.
Elsevier Science Publishers, "Nitric Oxide Related Interventions in Atherosclerosis", pp. 1181-1188, 2002.
Cho et al, XP-002304307, 2003-826115[77], 2003.
Takahashi et al, "Nitric Oxide Attenuates Adhesion Molecule Expression in Human Endothelial Cells", pp. 817-821, 1996.
Adams et al, "L-Arginine Reduces Human Monocyte Adhesion to Vascular Endothelium . . . ", pp. 662-668, 1997.

* cited by examiner

*Primary Examiner*—Johann R Richter
*Assistant Examiner*—Danielle Sullivan
(74) *Attorney, Agent, or Firm*—Dennison, Schultz & MacDonald

(57) ABSTRACT

The present invention, which is applicable in the pharmaceutical industry, relates to the use of molsidomine or one of its pharmaceutically acceptable salts, especially in the form of a sustained-release solid oral composition effective over 24 hours, for the manufacture of a drug for preventing or reducing the development of atherosclerosis.

6 Claims, 1 Drawing Sheet

SUSTAINED-RELEASE ORAL MOLSIDOMINE COMPOSITION FOR TREATING ATHEROSCLEROSIS

The present invention relates to a novel therapeutic use of molsidomine and its pharmaceutically acceptable salts, especially in a sustained-release oral galenical form effective over 24 hours, in the prevention or treatment of atherosclerosis.

Atherosclerosis is a progressive disease of the arteries which compromises the blood supply to the downstream organs. Thus the atheromatous plaques which appear on the wall of the coronary arteries are capable of restricting the blood supply to the heart (ischemia), which can lead to a myocardial infarction, the principal cause of death in industrialized countries.

Risk factors such as hypercholesterolemia or hypertension stimulate the formation of atherosclerotic lesions.

In the case of hypercholesterolemia, the mechanism leading to the formation of these lesions can be summarized as follows:

Low density lipoproteins (generally called LDL) accumulate in the tunica intima (innermost wall of the artery), where they are oxidized to Ox-LDL.

The presence of these oxidized molecules in the tunica intima causes the synthesis and expression of adhesion molecules such as ICAM-1 (intercellular adhesion molecule-1) and VCAM-1 (vascular cell adhesion molecule-1) on the surface of the endothelium.

These adhesion molecules have the property of fixing the monocytes originating from the bloodstream, which infiltrate the vascular wall and are transformed into macrophages.

These macrophages absorb the Ox-LDL (phagocytosis) and are thus transformed slowly into foam cells saturated with lipids. Furthermore, these macrophages release cytokines, which cause a local inflammatory reaction that favors an even more substantial recruitment of monocytes.

The smooth muscle cells multiply and migrate into the tunica intima, where they secrete collagen, elastic fibers and proteoglycans, leading to a progressive thickening of the lesions.

The foam cells also synthesize a tissue factor which participates in the deposition of fibrins in the atheromatous plaque, resulting in increasingly severe endothelial lesions.

As a consequence of the above, the adhesion molecules, particularly ICAM-1, are involved in the process of formation of the atherosclerotic lesions.

In fact, ICAM-1 is strongly overexpressed on the endothelium covering the atheromatous plaques in human coronary and carotid arteries.

Recent clinical studies indicate that the severity of atherosclerosis is correlated with the level of soluble ICAM-1 (hereafter ICAM-1s). Furthermore, in mouse atherosclerotic models, it has been observed that a depletion of ICAM-1s leads to a protective role against the progression of atherosclerosis.

A lowering of the levels of soluble ICAM-1 therefore seems to constitute an effective means of restoring the normal endothelial functions and preventing and/or slowing down the progression of atherosclerosis.

It is further known that molsidomine is a particularly useful compound in the preventive treatment of an angina attack in all its forms and acts by causing a relaxation of the vascular smooth muscle fiber and an inhibition of the early phases of platelet activation.

Molsidomine was initially marketed essentially:

in the form of immediate-release divisible tablets containing 2 mg and 4 mg doses, which were generally administered three times a day in the treatment of angina of effort and four times a day in the treatment of angina of rest and severe angina of effort; and then in the form of sustained-release tablets containing an 8 mg dose, which were to be administered twice a day for the long-term prophylactic treatment of angina pectoris.

More recently, molsidomine has been marketed (especially under the name Coruno® in Belgium) in the form of a sustained-release solid oral composition containing a 16 mg dose, effective over 24 hours, for the prevention and long-term chronic treatment of stable angina pectoris. The efficacy and tolerability of this composition have been demonstrated in a large number of patients in short-term and long-term studies.

It is in this context that it has been discovered, surprisingly and totally unexpectedly, that molsidomine, especially in the form of a sustained-release solid oral composition effective over 24 hours, makes it possible to restore the endothelial functions and thus to prevent the physiopathological processes that lead to atherosclerosis, and/or to slow down their progression.

More precisely, it has been discovered that the daily administration of such a galenical form of molsidomine substantially decreases the amount of circulating soluble ICAM-1, which is considered to be a biomarker of atherosclerosis, and that, in addition to its known antianginal properties, molsidomine thus makes it possible to inhibit the fixation of monocytes on the endothelium and consequently to ensure restoration of the endothelial functions and to prevent and/or slow down the progression of atherosclerosis.

Thus, according to a first feature, the present invention relates to the use of molsidomine or one of its pharmaceutically acceptable salts, especially in the form of a sustained-release solid oral composition effective over 24 hours, for the manufacture of a drug for preventing or attenuating the development of atherosclerosis.

Within the framework of the present invention, the molsidomine can be used in the free form, but also in the form of a pharmaceutically acceptable salt such as, in particular, a hydrochloride.

In the following description, the term molsidomine will be used to denote both the free form and the salified form of this molecule.

In general, in the treatment of atherosclerosis according to the invention, the molsidomine will be administered orally, especially in the form of sustained-release tablets effective over 24 hours.

The expression "effective over 24 hours" used here means that the amount of molsidomine released by the pharmaceutical form used is sufficient to produce a therapeutic plasma concentration of at least 5 ng/ml, preferably of at least 10 ng/ml, over a period of about 24 hours.

The effects of molsidomine in the treatment of atherosclerosis are particularly important within the framework of a long-term treatment (at least 6 months). These effects are particularly remarkable on stable angina patients.

Particularly valuable results in the treatment of atherosclerosis have been obtained according to the invention by the administration of sustained-release tablets containing a 16 mg dose, corresponding to the proprietary medicinal product Coruno® marketed in Belgium.

This galenical form and the process for its manufacture have been described in published US patent application 2003/0045522, which is incorporated here by reference.

In general, the galenical forms of molsidomine described in said international patent application are essentially characterized in that they have an in vitro dissolution rate [measured spectrophotometrically at 286 or 311 nm by the method described in the European Pharmacopoeia, 3rd edition (or USP XXIV), at 50 rpm, in 500 ml of a 0.1 N HCl medium, at 37° C.] of:
15 to 25% of molsidomine released after 1 hour
20 to 35% of molsidomine released after 2 hours
50 to 65% of molsidomine released after 6 hours
75 to 95% of molsidomine released after 12 hours
>85% of molsidomine released after 18 hours
>90% of molsidomine released after 24 hours, the plasma peak of molsidomine obtained in vivo occurring 2.5 to 5 hours, preferably 3 to 4 hours, following the administration of said form, and having a value of between 25 and 40 ng/ml of plasma.

In this context "the plasma peak of molsidomine obtained in vivo" corresponds to the mean maximum concentration of molsidomine found in the plasma of at least 10 healthy volunteers.

Within the framework of the present invention, any galenical form as described in said published US patent application 2003/0045522 can advantageously be used.

In general, these galenical forms make it possible to administer molsidomine in daily doses preferably of between 14 and 24 mg and particularly preferably of between 16 and 20 mg.

Such galenical forms of molsidomine, whose 24-hour release profile is characterized by the absence of close peaks and excessively pronounced troughs, prove particularly suitable in the treatment of atherosclerosis, guaranteeing a constant and stable release of the molsidomine at the sites affected by atherosclerosis.

Consequently, the relatively slow and constant release of molsidomine without pronounced and close plasma peaks seems to constitute an important characteristic for obtaining the desired effect in the treatment of atherosclerosis.

The use of molsidomine in these sustained-release galenical forms is particularly valuable insofar as this compound does not induce tolerance and the safety of its use has been demonstrated in a large number of patients.

DEMONSTRATION OF THE EFFECTS OF MOLSIDOMINE IN THE TREATMENT OF ATHEROSCLEROSIS

Figure 1:
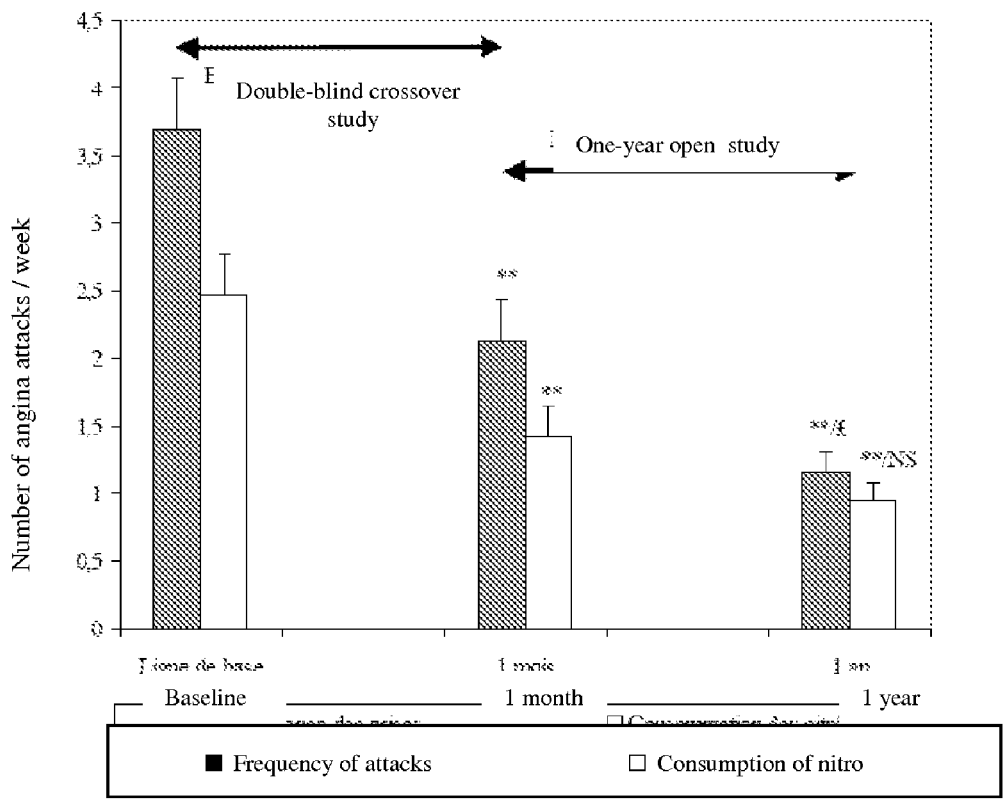
FIG. 1 is a graph showing the change in the weekly frequency of angina attacks and consumption of sublingual nitro tablets during the second and third phases of a study to be described.

1. Characteristics of the Population Studied and Study Design

The favorable effects of molsidomine in the treatment of atherosclerosis were demonstrated by a long-term clinical study conducted on 172 patients presenting with stable angina pectoris.

This study comprised 3 consecutive phases:
a 7-day pre-study under placebo;
a 4-week double-blind and double-placebo randomized crossover study during which the patients received alternately (2×2 weeks) a molsidomine-based formulation containing an 8 mg dose, currently marketed in Belgium under the name Corvatard® (2 daily dosage units), and a molsidomine-based formulation containing a 16 mg dose, effective over 24 hours, currently marketed in Belgium under the name Coruno® (1 daily dosage unit); and
a 12-month study during which the 172 patients received a molsidomine-based formulation containing a 16 mg dose, currently marketed in Belgium under the name Coruno®.

This study can be represented diagrammatically as follows:

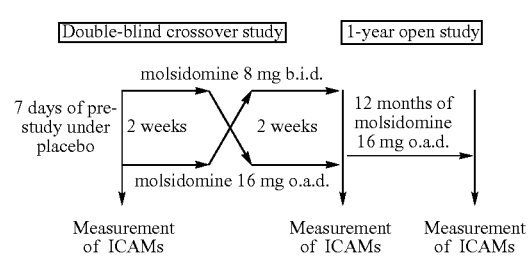

In this diagram and the description which follows, the abbreviation "b.i.d." (standing for "bis in die") is used to characterize the administration of molsidomine 8 mg in two daily dosage units, and the abbreviation "o.a.d." (standing for "once a day") is used to characterize the administration of molsidomine 16 mg in one daily dosage unit.

It is pointed out that, during the second phase of the study, the concomitant use of other antianginal drugs was prohibited with the exception of sublingual (s.l.) isosorbide dinitrate (ISDN) 5 mg in tablet form, which could be consumed ad libitum to alleviate the symptoms of anginal pain.

Furthermore, during the third phase of the study, the concomitant use of beta-blockers and/or calcium antagonists was authorized, while the use of oral nitro compounds and sildenafil was always prohibited.

Molsidomine 16 mg o.a.d. had to be taken orally every morning for one year.

The study was undertaken according to the clinical research guidelines for antianginal drugs supplied by the CPMP, in accordance with Good Clinical Practice (step 4) as applied in the European Community.

In the course of this study, the weekly frequency of angina attacks and the weekly frequency of consumption of s.l. ISDN 5 mg tablets were noted.

Also, and of greatest importance, the concentrations of ICAM-1s were measured after each of the three phases of the study, the first measurement constituting the baseline.

More precisely, the concentrations of ICAM-1s were measured as follows:

Blood samples (5 ml) were taken in non-heparinized tubes. These samples were kept at room temperature and then centrifuged. The serum was separated off and immediately frozen at −20° C. until required for analysis.

The circulating ICAM-1 was measured using a commercially available ELISA test (R&D Systems Europe).

2. Statistical Analyses

Descriptive statistics (means, standard deviation and %) were used to characterize the demography and the other parameters of the patient population of the study.

Analyses of variance for repeat measurements, with time as the classification criterion, followed by Bonferonni post-hoc tests when they were significant, were used to evaluate the change in the weekly frequency of angina attacks, the weekly consumption of s.l. nitro tablets and the levels of circulating ICAMs during the short-term part (second phase) and long-term part (third phase) of the study.

Student t tests or ANOVA with one classification criterion were used to evaluate the effects of sex, alcohol consumption, nicotine habits and the concomitant use of drugs on the levels of ICAMs measured after each phase of the study (pre-study baseline under placebo, after the four-week treatment and after the one-year treatment).

Analyses of variance for repeat measurements were used to evaluate the effects of the same risk factors on the change in the levels of ICAM-1s.

Pearson correlation coefficients were calculated in order to detect possible links between the levels of ICAM-1s and the continuous demographic variables or risk factors. The same method was employed to evaluate the correlations between the variations in the level of ICAM-1s and the changes in the risk factors.

Furthermore, the four quartiles of the changes in the level of ICAM-1s were determined after one year of treatment. An ANOVA test with one classification criterion, followed, when significant, by adjusted Bonferonni post-hoc tests, was used to determine the effects of the changes in the level of ICAM-1s, in the 4 categories thus defined (4 quartiles), on the changes observed (from the baseline to the end of the one-year treatment) in the weekly frequency of angina attacks and consumption of ISDN tablets.

3. Results

The demographic characteristics of the population at the baseline (taken from the pre-study under placebo) are detailed in Table 1.

TABLE 1

Demographic characteristics and baseline of patients participating in the study

| | N | Mean ± SD or % |
|---|---|---|
| Age (years) | 172 | 56.2 ± 8.3 |
| Duration of angina (years) | 172 | 4.4 ± 4.5 |
| Weight (kg) | 172 | 77.7 ± 12.0 |
| Weekly frequency of angina attacks | 107 | 3.7 ± 3.8 |
| Weekly frequency of consumption of ISDN tablets | 107 | 2.5 ± 3.2 |
| Diastolic blood pressure (mm Hg) | 172 | 82.0 ± 8.0 |
| Systolic blood pressure (mm Hg) | 172 | 131.2 ± 15.1 |
| Heart rate (beats/min) | 172 | 76.6 ± 11.0 |
| ICAM-1s (ng/ml) | 172 | 272 ± 92 |
| Sex | 172 | |
| Men | 117 | 68.0 |
| Women | 55 | 32.0 |
| Nicotine habits | 172 | |
| Non-smokers | 81 | 47.1 |
| Former smokers | 59 | 34.3 |
| Smokers | 32 | 18.6 |
| Concomitant treatment | 172 | |

TABLE 1-continued

Demographic characteristics and baseline of patients participating in the study

| | N | Mean ± SD or % |
|---|---|---|
| No other antianginal medication | 116 | 67.4 |
| Beta-blockers | 50 | 29.1 |
| Calcium antagonist | 2 | 1.2 |
| Both drugs | 4 | 2.3 |
| Alcohol consumption | 172 | |
| <1 glass/day | 161 | 93.6 |
| ≧1 glass/day | 11 | 6.4 |

SD = standard deviation

As shown in Table 1, the patients in the study were aged 56.2±8.3 years (mean±standard deviation), with males in the majority (68.0%), and had suffered from stable angina pectoris for an average of 4.4±4.5 years.

During the first phase of the study under placebo, preceding the active treatments, the weekly frequencies of angina attacks and consumption of ISDN tablets were respectively 3.7±3.8 attacks/week and 2.5±3.2 tablets/week.

Although the concomitant consumption of antianginal drugs had been authorized during this phase of the study, 67.4% of patients took no drugs other than molsidomine and 29.1% of patients took beta-blockers only.

FIG. 1 shows the change in the weekly frequency of angina attacks and consumption of sublingual nitro tablets during the second and third phases of the study.

The results are presented in the form of means±standard errors in the mean (SEM); ANOVA for repeat measurements, $p<0.0001$; Bonferonni post-hoc tests: ** comparisons versus baseline, $p<0.0001$; £ comparison between 4 weeks and one year, $p=0.002$; NS comparison between 4 weeks and one year, $p=0.105$.

As shown in FIG. 1, significant overall decreases in the weekly frequency of angina attacks and consumption of s.l. nitro tablets were measured ($p<0.0001$; ANOVA) during the study.

For the frequency of angina attacks, the differences were significant between the baseline and the 4-week treatment ($p<0.0001$; Bonferonni) and between the baseline and the one-year treatment ($p<0.0001$; Bonferonni). The differences were also significant between the 4-week treatment and the one-year treatment ($p=0.002$; Bonferonni).

For the consumption of s.l. nitro tablets, the differences were significant between the baseline and the 4-week treatment ($p<0.0001$; Bonferonni) and between the baseline and the one-year treatment ($p<0.0001$; Bonferonni).

Table 2 below shows the concentrations of ICAM-1s (ng/ml) measured during the short-term part (second phase) and long-term part (third phase) of the study, in particular to determine the influence of sex, alcohol consumption, nicotine habits and concomitant drugs on the change in the levels of circulating ICAM-1s.

TABLE 2

Change in the concentrations of ICAM-1s (ng/ml) during the short-term and long-term parts of the study, and influence of sex, alcohol consumption, nicotine habits and concomitant drugs

|  | N | Pre-study baseline under placebo Mean ± SD | 4 weeks double-blind Mean ± SD | One year open Mean ± SD | ANOVA Value of p (effect of time) | ANOVA Value of p (time-group interaction) |
|---|---|---|---|---|---|---|
| All patients | 172 | 272 ± 92 | 274 ± 87 | 246 ± 99$^{£/£}$ | <0.0001 | NA |
| Sex |  |  |  |  |  |  |
| Men | 117 | 264 ± 70 | 264 ± 58 | 236 ± 62$^{£/£}$ | <0.0001 | 0.914 |
| Women | 55 | 291 ± 126 | 293 ± 128 | 267 ± 149**$^{/£}$ | 0.001 |  |
| Alcohol consumption |  |  |  |  |  |  |
| <1 glass/day | 161 | 273 ± 94 | 276 ± 89 | 249 ± 102$^{£/£}$ | <0.0001 | 0.149 |
| ≧1 glass/day | 11 | 258 ± 63 | 242 ± 38 | 202 ± 25*$^{/**}$ | 0.003 |  |
| Nicotine habits |  |  |  |  |  |  |
| Non-smokers | 81 | 265 ± 86 | 262 ± 74 | 233 ± 70$^{£/£}$ | <0.0001 | 0.192 |
| Former smokers | 59 | 270 ± 71 | 277 ± 67 | 243 ± 63***$^{/£}$ | <0.0001 |  |
| Smokers | 32 | 295 ± 133 | 297 ± 138 | 282 ± 180 | 0.337 |  |
| Concomitant medication |  |  |  |  |  |  |
| None | 78 | 280 ± 117 | 276 ± 112 | 251 ± 132$^{£/£}$ | <0.0001 | 0.598 |
| Statins | 38 | 268 ± 74 | 277 ± 70 | 250 ± 79$^{NS/***}$ | <0.0001 |  |
| Beta-blockers | 30 | 276 ± 64 | 281 ± 58 | 243 ± 51$^{£/£}$ | <0.0001 |  |
| Both drugs | 20 | 246 ± 51 | 247 ± 45 | 222 ± 36 | 0.115 |  |

*/* = statistical probability versus baseline/versus 4-week results; Bonferonni post-hoc tests
* = p < 0.05;
** = p < 0.01;
*** = p = 0.001;
£ = p < 0.0001;
NS = not significant, p > 0.05;
NA = not applicable;
SD = standard deviation As shown in Table 2, the 4-week treatment with molsidomine (16 mg o.a.d. or 8 mg b.i.d.) had no effect on the levels of circulating ICAM-1s.

However, after 12 months of molsidomine 16 mg o.a.d., the levels of ICAM-1s were substantially (p<0.0001) lower (about 10%), compared with the baseline values before the crossover study.

The levels of circulating ICAM-1s tended to be higher in women than in men. However, the interaction with sex was not significant (p=0.914) by ANOVA, indicating that the decrease in ICAM-1s during the one-year treatment with molsidomine was parallel overall for both sexes.

Consumers of alcohol tended to show lower levels of ICAM-1s than non-consumers of alcohol. All the differences were not significant and the change in the level of ICAM-1s during the one-year treatment was parallel overall in both groups (p=0.149).

Smokers tended to have higher levels of ICAM-1s than non-smokers or former smokers, but once again the change in the level of ICAM-1s was the same overall, irrespective of nicotine habits (p=0.192).

The use of concomitant drugs such as statins, beta-blockers or a combination of both had no influence on the level of ICAM-1s. All the differences were not significant and the change in the level of ICAM-1s was independent of the type of concomitant drug absorbed during the one-year treatment period (p=0.598).

At the baseline there was no correlation between the concentrations of ICAM-1s and the demographic factors or risk factors such as age (r=−0.068), weight (r=−0.079), duration of stable angina (r=0.042), weekly frequency of angina attacks (r=0.137), weekly frequency of consumption of s.l. ISDN tablets (r=0.124), diastolic blood pressure (r=0.051), systolic blood pressure (r=0.097) or heart rate (r=0.176).

The same conclusions could be drawn as regards the correlations between the variations in the level of ICAM-1s and the changes in the demographic factors and risk factors after a one-year treatment with molsidomine (data not shown).

Figure 2:
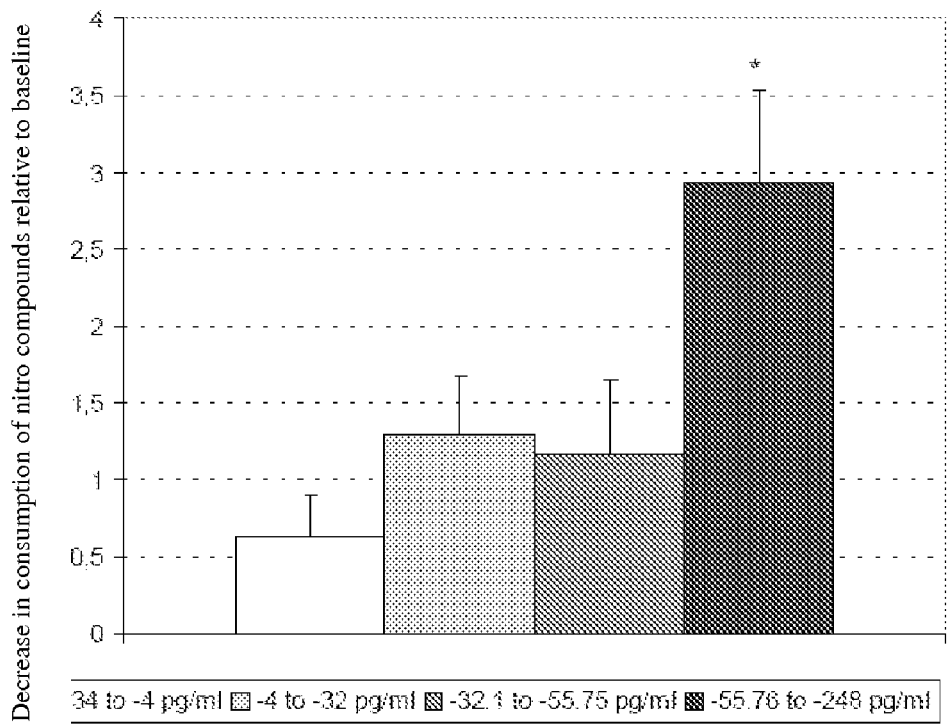
FIG. 2 shows the decrease in the weekly frequency of consumption of ISDN tablets as a function of the variation in the level of circulating ICAM-1s after a one-year treatment with molsidomine 16 mg o.a.d.

FIG. 2 shows the decrease in the weekly frequency of consumption of ISDN tablets as a function of the variation in the level of circulating ICAM-1s after a one-year treatment with molsidomine 16 mg o.a.d.; the 4 categories of changes in ICAM-1s correspond to the 4 distribution quartiles.

The results are presented in the form of means±standard errors in the mean (SEM); ANOVA, p=0.031; * Bonferonni post-hoc tests, p=0.038.

FIG. 2, with the distribution in four quartiles of the changes in the levels of ICAM-1s during the third phase of the study, shows that the effect of the change in the level of ICAM-1s on the change in the frequency of consumption of s.l. ISDN tablets was significant (p=0.031).

The Bonferonni post-hoc tests demonstrated that the decrease in the consumption of ISDN between the beginning and end of the third phase of the study (12 months later) was more pronounced in the group showing the greater decrease in ICAM-1s (4th distribution quartile) (p=0.038).

The same tendency was measured for the change in the weekly frequency of angina attacks, but the differences between the 4 quartiles of changes in ICAM-1s were not significant (p=0.072) (data not shown).

4. Discussion

The present study made it possible to evaluate the effect of a short period (4 weeks) and a long period (one year) of treatment with molsidomine 16 mg o.a.d. in patients presenting with stable angina pectoris.

Surprisingly, the results obtained show that, after administration of this galenical form for one year, the significant antianginal effects already measured after a 4-week treatment persist, and that the levels of circulating ICAM-1s (a proinflammatory marker of endothelial dysfunction and a potential therapeutic target in the pathology of atherosclerosis) are substantially reduced.

At the beginning of the study, after a seven-day pre-study period under placebo, the levels of ICAM-1s were comparable to the values obtained in other studies in patients suffering from coronary heart disease or stable angina. Women and established smokers tended to have higher levels than men and non-smokers or former smokers, confirming the observations of earlier studies.

The short-term treatment (4 weeks) with molsidomine did not cause any effect on the levels of circulating ICAM-1. In these patients presenting with stable angina, however, the efficacy of the 4-week antianginal treatment was significant inasmuch as the number of angina attacks and the consumption of sublingual nitro compounds decreased.

After 12 months of molsidomine 16 mg o.a.d., the levels of ICAM-1s were substantially lower. This decrease was independent of other parameters such as sex, alcohol consumption, nicotine habits or concomitant medication. After one year, the antianginal effects of molsidomine were maintained or even improved and the most pronounced decrease in consumption of sublingual nitro compounds was observed in patients showing the greatest decrease in the levels of ICAM-1s (4th quartile).

In conclusion, the reduction in the ICAM-1s marker after a one-year treatment with molsidomine 16 mg o.a.d. indicates that, in addition to its antianginal function, this compound favors a less activated state of the endothelium and therefore makes it possible to prevent and/or slow down the progression of atherosclerosis, especially in patients presenting with stable angina pectoris.

The invention claimed is:

1. A method for attenuating development of atherosclerosis comprising administering molsidomine or one of its pharmaceutically acceptable salts daily, for a period of at least six months, in the form of a sustained-release solid oral composition containing between 14 and 24 mg of molsidomine effective over 24 hours.

2. A method according to claim 1, wherein the sustained release oral composition effective over 24 hours has an in vitro dissolution rate, measured spectrophotometrically at 286 or 311 nm by the method described in the European Pharmacopoeia, 3rd edition (or USP XXIV), at 50 rpm, in 500 ml of a 0.1 N HCl medium, at 37° C., of:

15 to 25% of molsidomine released after 1 hour
20 to 35% of molsidomine released after 2 hours
50 to 65% of molsidomine released after 6 hours
75 to 95% of molsidomine released after 12 hours
>85% of molsidomine released after 18 hours
>90% of molsidomine released after 24 hours, the plasma peak of molsidomine obtained in vivo occurring 2.5 to 5 hours following the administration of said form, and having a value of between 25 and 40 ng/ml of plasma.

3. A method according to claim 2, wherein said plasma peak of molsidomine obtained in vivo occurs 3 to 4 hours following the administration of said form.

4. A method according to claim 1, wherein said solid oral composition contains 16 mg of molsidomine per dosage unit intended for daily administration.

5. A method according to claim 1, wherein said solid oral composition is administered to a patient suffering from angina pectoris.

6. A method according to claim 2, wherein said solid oral composition is administered to a patient suffering from angina pectoris.

* * * * *